United States Patent [19]
Aldridge

[11] Patent Number: 5,157,790
[45] Date of Patent: Oct. 27, 1992

[54] FIREFIGHTER GARMENT WITH LUMBAR SUPPORT
[75] Inventor: Donald Aldridge, New Carlisle, Ohio
[73] Assignee: Lion Apparel, Inc., Dayton, Ohio
[21] Appl. No.: 780,151
[22] Filed: Oct. 21, 1991
[51] Int. Cl.[5] ............................................. A41D 1/06
[52] U.S. Cl. .......................................... 2/227; 2/81; 2/255
[58] Field of Search ................... 2/69, 79, 81, 82, 227, 2/229, 230, 231, 234, 235, 236, 237, 255, 256; 450/103, 143; 602/13, 19

[56] References Cited
U.S. PATENT DOCUMENTS

| | | | |
|---|---|---|---|
| 2,372,034 | 3/1942 | Versoy | 128/96 |
| 2,501,900 | 3/1950 | Herbener | 2/255 |
| 2,815,023 | 7/1955 | Hammersley | 128/99 |
| 3,141,457 | 7/1963 | Davidson | 128/95 |
| 3,422,461 | 1/1969 | Froehlich | 2/255 |
| 4,022,197 | 5/1976 | Castiglia | 128/101 |
| 4,143,663 | 3/1979 | Williams | 450/103 |
| 4,794,916 | 11/1986 | Porterfield et al. | 128/78 |
| 4,976,653 | 12/1990 | White | 2/221 |
| 4,991,573 | 3/1990 | Miller | 128/78 |
| 5,036,548 | 8/1991 | Grilliot | 2/227 |
| 5,046,488 | 9/1991 | Schiek | 2/338 |
| 5,050,244 | 9/1991 | Kleinman | 2/227 |

Primary Examiner—Werner H. Schroeder
Assistant Examiner—Diana L. Biefeld
Attorney, Agent, or Firm—Thompson, Hine and Flory

[57] ABSTRACT

A firefighter garment having an outer shell with a waist portion covering a lower back area of a wearer and a front closure, an inner liner having a thermal layer and shaped to fit within the outer shell and a support member, attached to the outer shell, for supporting a lumbar region of the wearer. The support member preferably includes a plurality of elastic bands extending about the waist portion of the garment and having complementary closure members positioned adjacent to the front closure of the outer shell, and a contact member, attached to the elastic straps, positioned to contact the lumbar region of the wearer. In one embodiment, the elastic straps are integral with the garment, preferably a pant, and in another embodiment, the support member comprises a girdle which is attachable to the firefighter pant and includes buttons for attachment to suspenders, thereby forming a component of a pant suspension system. In one embodiment, the contact member consists of a resilient pad centered in the lumbar area of the wearer, and in another embodiment, the contact member consists of a plurality of elongate, vertically-extending stays.

35 Claims, 3 Drawing Sheets

FIREFIGHTER GARMENT WITH LUMBAR SUPPORT

BACKGROUND OF THE INVENTION

The present invention relates to firefighter garments and, more particularly, firefighter garments having orthopedic components for reducing the strain of a wearer when encountering heavy loads.

A typical firefighter garment includes a pant and jacket, each having an outer shell of a fire-resistant material such as an aramid fiber (NOMEX and KEVLAR brand aramid fibers, both products of E. I. DuPont de Nemours & Co., Inc.) and an inner liner having a moisture barrier component and a thermal barrier component. The moisture barrier may be FORTEX material (a trademark of W. L. Gore & Associates, Inc.) and the thermal barrier may be a felt of aramid fibers. The inner liner components typically are quilted together, and the inner liner is separable from the outer shell to facilitate laundering of the garment.

The firefighter pant typically is beltless and is held in position by suspenders which fit under the jacket. The inner pant liner and outer pant shell snap or button together and the suspender ends or tabs may attach to such buttons or snaps, or may be attached by separate means. Both the jacket and the pant are loose fitting and somewhat baggy to allow freedom of movement.

While such firefighter garments provide adequate protection against such hazards as heat, water and flash flame, they provide no protection for the hazard of muscle strain, especially in the lumbar region of the spine of the wearer. In the fighting of fire, the firefighter is called upon to carry heavy equipment, such as hoses and ladders, over his shoulder, and occasionally is required to carry an injured person over his shoulder in the well-known "firemen's carry" maneuver. In addition, the firefighter often carries a tank of breathing air strapped to his back. All of these items and activities impose a stress upon the lumbar region of the back which is often an unbalanced imposition of a weight load.

While there are many types of designs for so-called lumbar stabilizers, such as the stabilizer disclosed in Porterfield, et. al. U.S. Pat. No. 4,794,916 and Miller U.S. Pat. No. 4,991,573, such devices are designed to provide comfort and reduce stress to an individual who has sustained an injury in the lumbar area of the spine. It is not an object of such devices to provide a prophylactic benefit to a wearer in the hazardous environment of a firefighter. Further, such devices are designed to be worn independently of any other type of garment and typically are worn underneath the outer garments of a wearer.

It is impractical to require firefighters to keep track of and separately put on such lumbar stabilizers, in addition to all of the other firefighter garments and gear, in the rush to answer an alarm. Accordingly, there is a need for a firefighter garment which provides support for a firefighter in the lumbar region of the wearer's spine in order to minimize the risk of injury to that region sustained during strenuous firefighting activity.

SUMMARY OF THE INVENTION

The present invention is a firefighter garment with a support which minimizer the stress imposed upon the lumbar region of the spine of the wearer, thereby reducing the likelihood of spinal and muscle injury to firefighters in the course of firefighting activities. The support is integral with the garment and can be selectively activated and deactivated so that the support feature is applied only when needed. Another benefit of the invention is the so-called "placebo effect," wherein the mere presence of the invention in a firefighter garment makes the wearer self-conscious of his lifting form, and serves to encourage use of good lifting form.

In a preferred embodiment of the invention, the garment is a firefighter pant having an inner liner with a thermal layer and an outer shell having a waist portion covering the lower back area of the wearer, including the lumbar region, and a support member, attached to the shell, for supporting the lumbar region of the wearer. The support member includes a plurality of elastic bands which encircle the waist of the wearer and includes a closure mechanism in the front of the wearer adjacent to the pant closure. The elastic bands support a contact member positioned adjacent the lumbar region of the spine, which ensures proper alignment of the lumbar vertebrae during bending and lifting. In one embodiment, the contact member is a pad positioned over the lumbar vertebrae and in another embodiment, stays extend vertically in parallel with the lumbar vertebrae.

The closure member of the elastic bands allows the wearer support the closure member by connecting the closure member, thereby applying a radially inward pressure against the lumbar region, or deactivate the support member by disconnecting the closure member to relax the elastic bands. Accordingly, the support member be comfortably all times and activated only when needed during strenuous firefighting activity.

In an alternate embodiment, the support member includes a girdle made of shell material which encloses the waist of the wearer in the lumbar region and includes inner and outer layers in closing the elastic bands. The girdle includes buttons for connecting to suspenders, and button holes or snaps for connection to the firefighter pant, thereby acting as an integral component of the pant suspension system. Such a girdle is therefore retrofittable to existing firefighter pants. The girdle includes a front closure member, separate from the elastic bands, so that the girdle may be worn comfortably at all times, and the elastic bands adjusted activate it when needed.

In all of the embodiments, it is preferable to provide closure members consisting of complementary strips of hook and loop material. However, other closure members, such as buckles, snaps and hook-and-D connectors may be used.

Accordingly, it is an object of the present invention to provide a firefighter garment with an integral lumbar support mechanism; a firefighter garment with a lumbar support mechanism which be activated and de-activated as needed to ensure wearer comfort at all times; a firefighter garment with integral lumbar support mechanism for a firefighter garment which does not add significantly to the weight of the firefighter garment; a firefighter garment with a lumbar support mechanism which is relatively easy to activate and de-activate as needed; and a firefighter garment with a lumbar support mechanism which is relatively inexpensive to incorporate into the garment, or can be provided as an integral component retrofitted to an existing garment design.

Other objects and advantages of the present invention will be apparent from the following description, the accompanying drawings and the appended claims.

DETAILED DESCRIPTION

Figure 1:
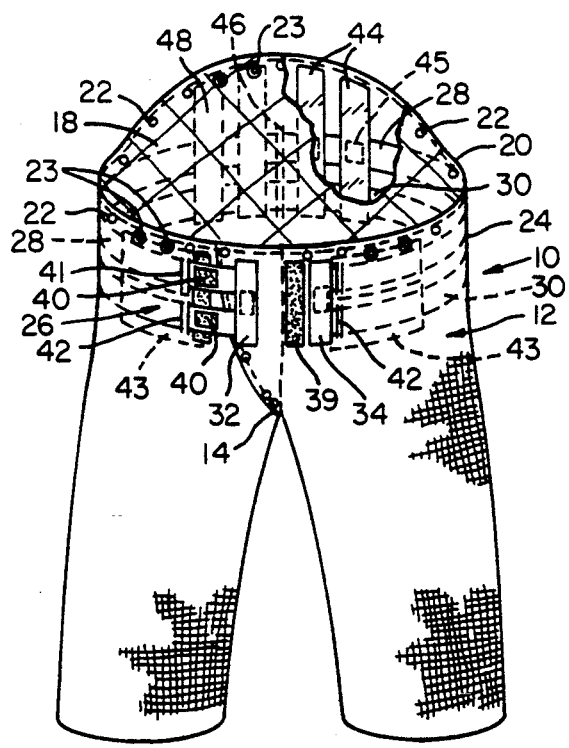
FIG. 1 is a somewhat schematic, perspective view of a firefighter pant embodying the present invention.
Figure 2:
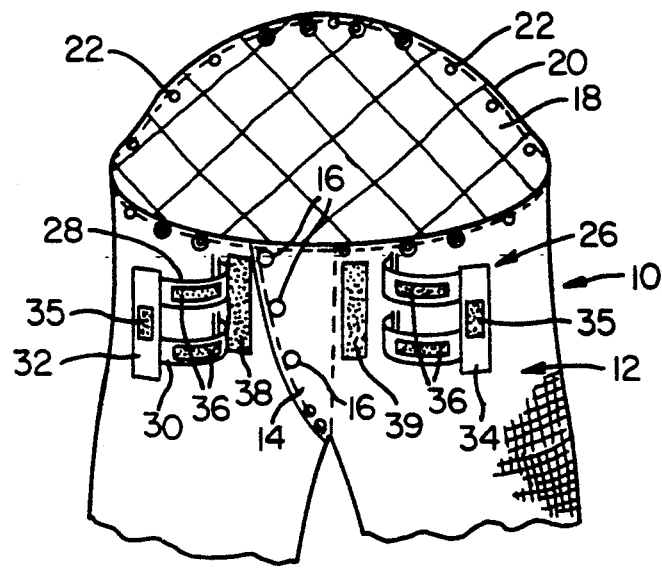
FIG. 2 is a detail of the pant of FIG. 1, showing the underside of the ends of the straps.

As shown in FIGS. 1 and 2, the firefighter garment of the present invention, generally designated 10, is a pant having an outer shell 12 made of a woven aramid fiber such as NOMEX or KEVLAR. The outer shell includes a front closure 14 which is secured by snaps 16. The pant 10 includes an inner liner 18 having an outer moisture barrier quilted to a batting of NOMEX fibers. The inner liner 18 is shaped to fit within the outer shell 12 and is attached to the outer shell at the waistline 20 by snaps 22. The liner 18 includes suspender buttons 23 which protrude through the shell 12.

The waist portion 24 of the garment includes a support member, generally designated 26. The support member includes upper and lower elastic straps 28, 30, respectively. The waist portion 24 and support member 26 are positioned on the pant 10 to encircle the midriff of a wearer, and the rear portion of the support member is positioned to lie adjacent to the lumbar region of the spine of the wearer.

Adjacent ends of the straps 28, 30 are connected by closure tabs 32, 34, and each of the tabs has attached to its underside a hook component 35 of a hook and loop closure mechanism. Similarly, straps 28, 30 include strips 36 of hook material. The outer shell 12 includes complementary strips 38, 39 loop material, and the outer surfaces of the straps 28, 30 adjacent tabs 32, 34 include squares 40 of loop material (see also FIG. 4).

The straps 28, 30 extend through slits 41, 42 formed in the outer shell which, at the waist portion 24, includes inner retainer squares 43 of shell material stitched to the outer shell. The portions of straps 28, 30 extending between slits 41, 42 extend between the squares 43 and shell 12. The straps 28, 30 support a plurality of oblong, vertically-extending stays 44, secured by hook and loop connections 45 to the radially inner surface of the straps. The straps preferably are made of a rigid plastic material such as nylon. The straps 28, 30 are secured to the rear of the waist portion 24 by stitching 46 and the stays 44 are positioned to lie on either side of the lumbar vertebrae of a wearer.

As shown in FIG. 1, the rear portion 48 of the waist portion 24 of the pant 10 is raised, relative to the front portion of the pant, to ensure that a sufficient portion of the lumbar region of the wearer is contacted by the stays 44.

Figure 4:
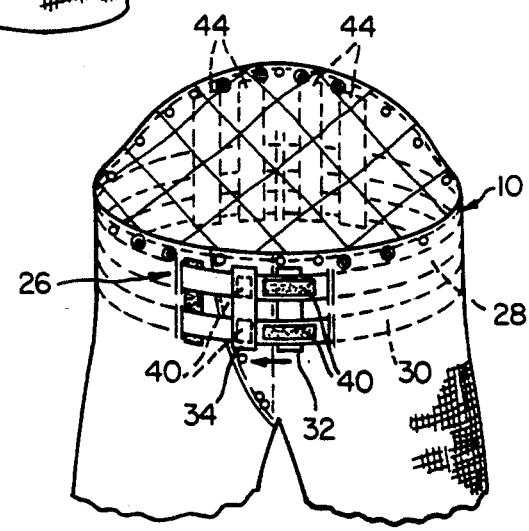
FIG. 4 is the detail of FIG. 3 showing the support member fully activated.
Figure 3:
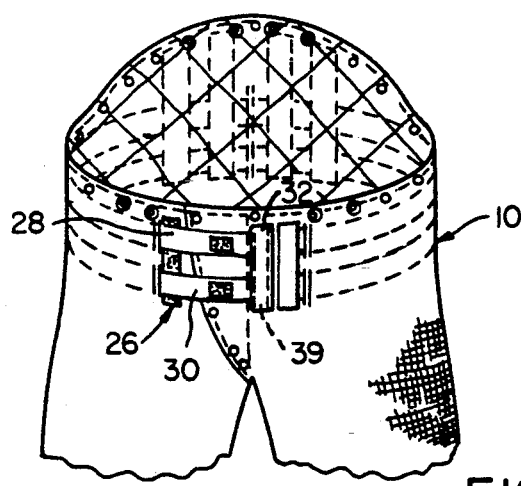
FIG. 3 is a detail of the pant of FIG. 1 showing an end of the support member attached to the pant in the first step of activation.

The method of activating the support member 26 is shown sequentially in FIGS. 1, 3, and 4. FIG. 1 shows the support member in a de-activated configuration; that is, the tabs 32, 34 are not attached to each other and accordingly, the straps 28, 30 do not exert an inward constrictive force on the mid-section of a wearer. Preferably, tabs 32, 34 are attached to panels 38 of loop material adjacent to slits 41, 42 (see FIG. 2).

As shown in FIG. 3, in order to activate the support member 26, tab 32 is brought over to panel 39 so that the panels 35 and/or 36 on tab 32 and/or straps 28, 30 (see FIG. 2) contact panel 39, thereby attaching the tab to the pant 10 at the position of panel 39. Next, as shown in FIG. 4, tab 34 is superposed to squares 40 so that panel 36 on tab 34 is brought into contact with the squares 40 to make a connection and fix the tab 34 relative to the squares. Accordingly, the pant 10 shown in FIG. 4 is in an activated configuration in which the ends of the straps 38, 30 are in an overlapping relation and are tightened about the waist of a wearer, thereby urging the stays 44 into the lower back of the wearer in the lumbar region, preferably on either side of the lumbar vertebrae. This constrictive pressure supports the back of the wearer and reduces the likelihood of back injury due to heavy or unbalanced lifting.

The adjustment of the support member 26 from the activated configuration shown in FIG. 4 to the de-activated configuration shown in FIG. 1 is simply the reverse of the aforementioned steps. The tab 34 is pulled away from the straps 28, 30, thereby separating the hook and loop panels from each other, and the tail is allowed to retract to its normal position. Tab 32 is then separated from the shell 12, thereby separating the hook and loop closure panels on the tab and pant shell 12 at that point, and straps 28, 30 are allowed to retract t their unstretched positions. The tabs 32, 34 then assume the configuration shown in FIG. 1. It is anticipated that a firefighter wearing the pant 10 of the present invention would wear the pant principally in a de-activated configuration, as shown in FIG. 1, then adjust the support member 26 to the activated configuration of FIG. 4 before fighting a fire or engaging in heavy lifting.

Figure 5:
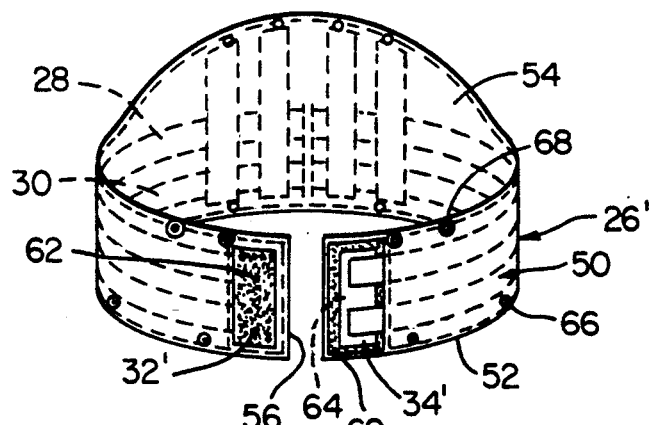
FIG. 5 is a detail of an alternate embodiment of the invention showing a girdle incorporating the support member.
Figure 6:
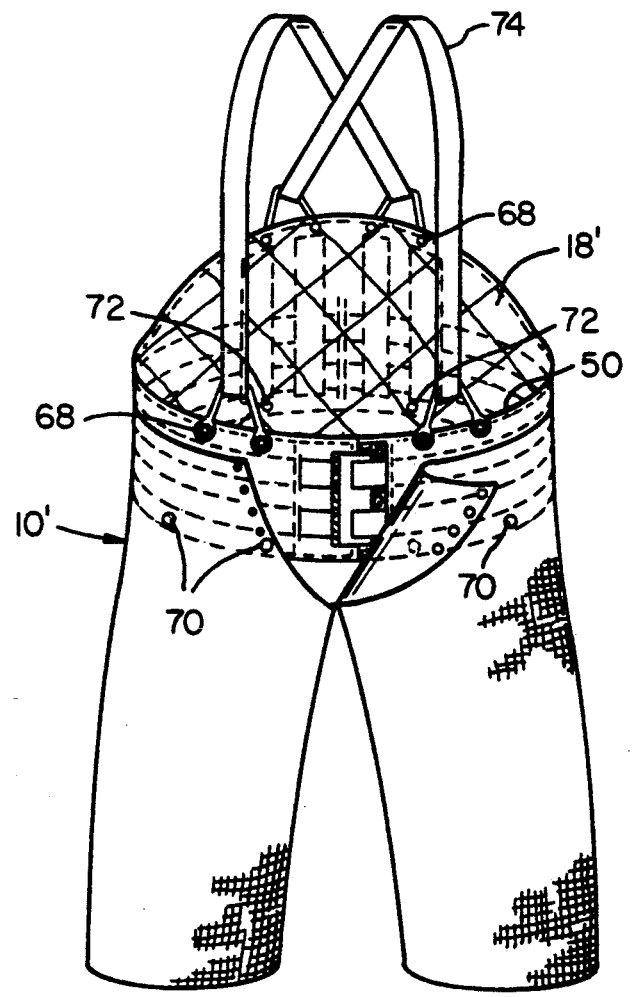
FIG. 6 is the alternate embodiment of the invention of FIG. 4

An alternate embodiment of the invention is shown in FIGS. 5 and 6. In FIG. 5, the support member 26' includes a girdle 50 made of inner and outer layers 52, 54 of shell material stitched together at their peripheries. The girdle 50 includes a front closure 56 which includes complementary panels 58, 60 of hook and loop material to secure the girdle when worn.

The straps 28, 30 are attached at their ends to tabs 32', 34', each of which has a panel of hook and loop material 62, 64 attached to it.

The girdle 50 includes snaps 66 about its lower periphery and suspender buttons 68 attached to about its upper periphery. As shown in FIG. 6, the girdle 50 is attached to a firefighter pant 10' by engagement of the girdle with complementary snaps 70 mounted on the outer shell and complementary snaps 72 mounted on the inner liner 18'. A pair of standard firefighter suspenders 74 are then attached to the buttons 68 of the girdle 50 to complete the pant 10' construction.

In order to activate the girdle 50, panel 32' is stretched to contact the exposed portion of panel 58 of the girdle and is attached by means of the hook and loop connection between those components. The tab 34' is then stretched and attached to the back side of tab 32' so that the complementary hook and loop panels of those components engage. When this connection is effected, the stays 44 are urged into the lumbar region of the back of the wearer by the constrictive force of the straps 28, 30.

Figure 7:
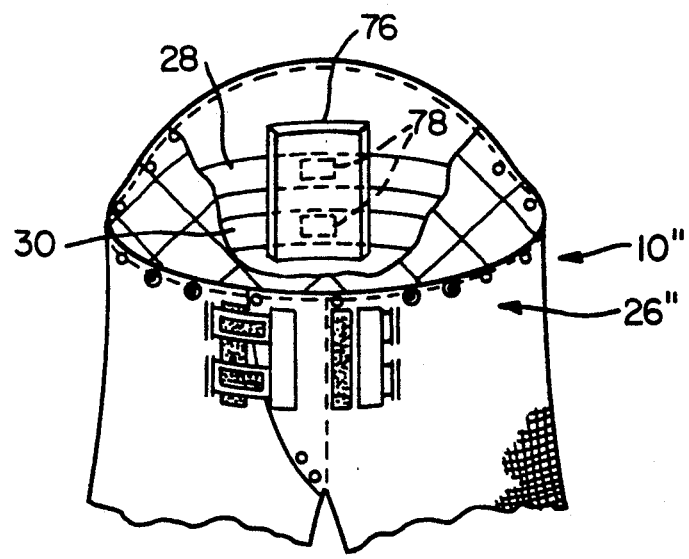
FIG. 7 shows an alternate embodiment of the invention in which the pant of FIG. 1 has been modified to include a pad.

A second alternate embodiment 10" having a modified support member 26" is shown in FIG. 7. In this embodiment, the support member 26" is identical in all respects to the support member 26 of FIGS. 1-4, except that the stays 44 have been replaced by a lumbar pad 76. The lumbar pad 76 is made of a thick, hard foam and is approximately 8 inches long, 6 inches wide, and ½ inch thick. The pad 76 is attached by hook and loop connections 78 to the straps 28, 30 of the support member 26". Accordingly, when the support member 26" of the pant 10" shown in FIG. 7 is activated, the straps 28, 30 urge the pad 76 into the lumbar vertebrae of the wearer to provide support for lifting and bending movement.

It should be noted that the preferred embodiment of the invention shows a support member which is integral or unitary with a firefighter pant. It is within the scope of the invention to provide a support member which is unitary or integral with the jacket portion of a firefighter garment. Further, other closure means may be used to adjust the support member to an activated configuration. For example, the hook and loop attachment panels may be replaced with other mechanical attachment mechanisms such as a perforated belt and buckle or a hook and D connection. However, the hook and loop connection is preferred because of the ease of attachment and removal.

While the forms of apparatus herein described constitute preferred embodiments of this invention, it is to be understood that the invention is not limited to these precise forms of apparatus, and that changes may be made therein without departing from the scope of the invention.

What is claimed is:

1. A firefighter garment comprising:
   an outer shell having a waist portion covering a lower back area of a wearer and front closure means;
   an inner liner having a thermal layer and shaped to fit within said outer shell; and
   means for supporting a lumbar region of a wearer, said support means being attached to said shell.

2. The garment of claim 1 wherein said support means includes resilient means for urging said support means against said lumbar region.

3. The garment of claim 2 wherein said resilient means includes support closure means for selectively activating said resilient means to urge said support means against said lumbar region, and deactivating said resilient means whereby said support means is not urged into said lumbar region.

4. The garment of claim 3 wherein said resilient means includes elastic strap means extending about said waist portion.

5. The garment of claim 4 wherein said support closure means is positioned adjacent to said front closure means.

6. The garment of claim 5 wherein said elastic strap means extends through said waist portion.

7. The garment of claim 6 wherein said support means includes a contact member, attached to said elastic strap means and positioned to contact said lumbar region when said support means is activated.

8. The garment of claim 7 wherein said contact member includes a resilient pad.

9. The garment of claim 7 wherein said contact member includes a plurality of vertically-oriented, elongate stays.

10. The garment of claim 7 wherein said garment is a pant.

11. The garment of claim 7 wherein said support means includes a girdle, said girdle having means about a lower periphery- thereof for attachment to 12. The garment of claim 11 wherein said girdle includes means for attachment to pant support means.

13. The garment of claim 12 wherein said pant support means includes suspenders.

14. A firefighter pant comprising:
   an outer shell having a waist portion covering a lower back area of a wearer and front closure means;
   an inner liner having a thermal layer and being shaped to fit within said outer shell; and
   means for supporting a lumbar region of a wearer of said pant, said support means being integral with said shell.

15. The pant of claim 14 wherein said support means includes resilient means for urging said support means against said lumbar region.

16. The pant of claim 15 wherein said resilient means includes support closure means for selectively activating said resilient means to urge said support means against said lumbar region, and deactivating said resilient means whereby said support means is not urged into said lumbar region.

17. The pant of claim 16 wherein said support closure means includes first fastening means attached to ends of said resilient means; and second, complementary fastening means attached to said pant adjacent one of said resilient means ends and on an outer surface of the other of said resilient means ends, whereby activation of said support means is effected by engagement between said first and second fastening means.

18. The pant of claim 17 wherein said fastening means include hook and loop fasteners.

19. The pant of claim 18 wherein said support closure means is positioned adjacent to said front closure means of said pant.

20. The pant of claim 19 wherein said resilient means includes a lumbar contact member positioned to contact said lumbar region when said support means is activated.

21. The pant of claim 20 wherein said contact member includes a pad.

22. The pant of claim 20 wherein said contact member includes a plurality of vertically-extending, elongate stays.

23. The pant of claim 20 wherein said resilient means includes a plurality of elastic straps extending through said waist portion.

24. A firefighter pant comprising:
   an outer shell having a waist portion covering a lower back area of a wearer and front closure means;
   an inner liner having a thermal layer and shaped to fit within said outer shell; and
   removable means for supporting a lumbar region of a wearer of said pant.

25. The pant of claim 24 wherein said support means includes a girdle attachable to said outer shell.

26. The pant of claim 25 wherein said girdle includes pant support means.

27. The pant of claim 26 wherein said pant support means includes suspenders.

28. The pant of claim 25 wherein said girdle includes elastic means for urging said support means into said lumbar region.

29. The pant of claim 28 wherein said elastic means includes a plurality of elastic straps.

30. The pant of claim 29 wherein said girdle includes girdle closure means.

31. The pant of claim 30 wherein said elastic means includes complementary closure means at ends thereof, said complementary closure means being joined to urge said support means into said lumbar area in an activated configuration, and separated to relax said support means in a deactivated configuration.

32. The pant of claim 31 wherein said girdle includes inner and outer layers of shell material, said elastic straps being enclosed by said inner and outer layers.

33. The pant of claim 32 wherein said elastic means includes a contact member positioned to contact said lumbar region when said support means is activated.

34. The pant of claim 33 wherein said contact member includes a resilient pad.

35. The pant of claim 34 wherein aid contact member includes a plurality of vertically-oriented, elongate stays.

* * * * *